United States Patent [19]

Sims

[11] Patent Number: 4,685,153
[45] Date of Patent: Aug. 11, 1987

[54] ATHLETIC KNEE PROTECTOR

[76] Inventor: Leon Sims, 4709 California St., Omaha, Nebr. 68132-2503

[21] Appl. No.: 866,900

[22] Filed: May 27, 1986

[51] Int. Cl.⁴ .................. A61E 13/06; A41D 13/06
[52] U.S. Cl. ..................................... 2/24; 128/89 R
[58] Field of Search ............... 2/22, 23, 24; 128/80 C, 128/89 R

[56] References Cited

U.S. PATENT DOCUMENTS

| 563,468 | 7/1896 | Fergusson | 2/24 |
|---|---|---|---|
| 1,789,798 | 1/1931 | Wineland | 2/24 |
| 2,338,424 | 1/1944 | Giardini | 2/22 |
| 2,650,362 | 9/1953 | Musgrave | 2/24 |
| 3,465,365 | 9/1969 | Jones et al. | 2/24 |
| 3,670,339 | 6/1972 | Cooper et al. | 2/22 |
| 3,938,509 | 2/1976 | Barber | 128/89 R |
| 3,942,522 | 3/1976 | Wilson | 128/89 R |
| 4,024,584 | 5/1977 | Smith | 2/24 |
| 4,035,844 | 7/1977 | Atack et al. | 2/22 X |
| 4,041,940 | 8/1977 | Frankel et al. | 2/24 X |
| 4,198,708 | 4/1980 | Fugere et al. | 2/16 |
| 4,250,578 | 2/1981 | Barlow | 2/24 |
| 4,274,402 | 6/1981 | Shippert | 128/89 R |
| 4,296,744 | 10/1981 | Palumbo | 2/24 X |
| 4,333,181 | 6/1982 | Corriero | 128/80 C |
| 4,387,709 | 6/1983 | Shen | 128/80 C |
| 4,425,912 | 1/1984 | Harper | 2/24 X |

FOREIGN PATENT DOCUMENTS

| 3416253 | 11/1985 | Fed. Rep. of Germany | 128/80 C |
|---|---|---|---|
| 2553996 | 5/1985 | France | 128/80 C |

Primary Examiner—Louis K. Rimrodt
Attorney, Agent, or Firm—E. Robert Newman

[57] ABSTRACT

An athletic knee protector having a flexible aluminum shield which wraps around the kneecap and sides of the knee and is held in place at the kneecap by fitting within a pocket sewn within stretch pants and by having straps which are attached to the pants interior from above the pocket, brought through an opening in the pants centered below the pocket, and then secured by wrapping about the leg and foot and tied together at knee level.

3 Claims, 5 Drawing Figures

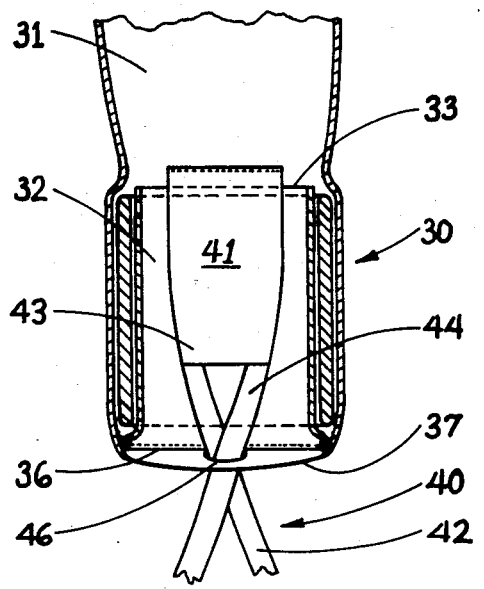
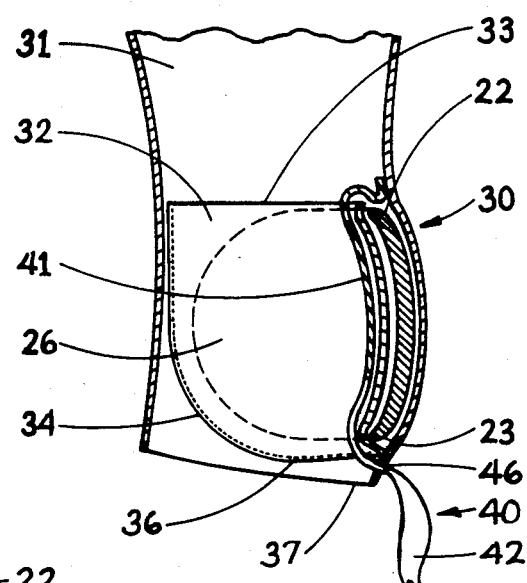
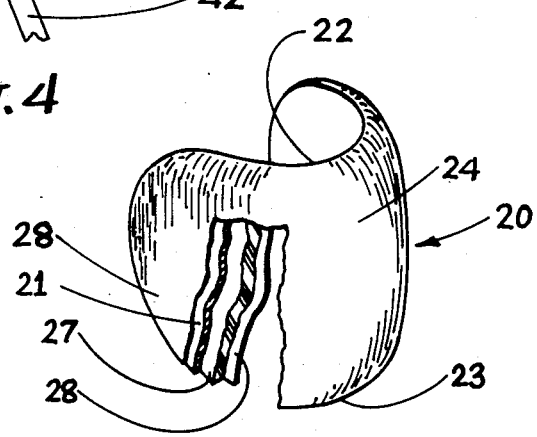
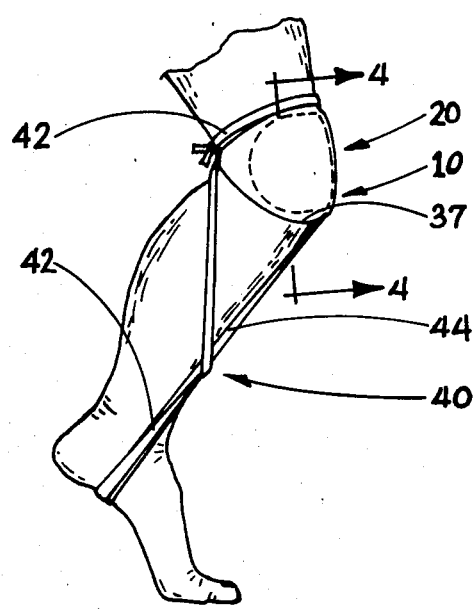
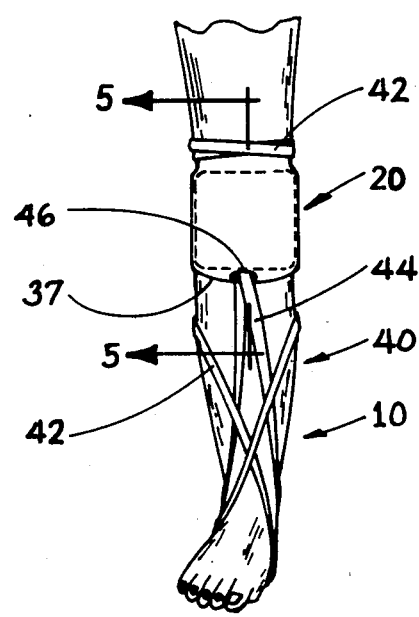

ATHLETIC KNEE PROTECTOR

TECHNICAL FIELD

The present invention relates generally to devices for protecting the knee while in athletic endeavors, and more particularly to such devices which include a rigid protective member and structure for holding it in place.

BACKGROUND ART

Serious damage caused by hard blows and extreme twisting frequently occurs to an athlete's knee in various contact sports. This is particularly true of the game of American football. Despite the frequency and severity of such accidents, most technological progress in recent years has been in post-injury protective devices and in surgical procedures. Devices or equipment designed to prevent such injury are generally not available or inadequate under severe circumstances.

The steel hinge which straps to the leg above and below the knee is well known. However, its use has been largely limited to two situations. One is for use by those who have suffered injury, but not so severly that surgery cannot wait until after remaining games in the season are played. The other is for use by those whose surgery is recent enough that cautionary protection is warranted. The reasons for these limits are that such devices are quite restrictive in terms of the amount of knee flex permitted and the degree of flexibility remaining while in place. Additionally, the steel knee hinge is heavy and it allows almost no lateral bending.

Protection against torn knee ligaments and kneecap damage is, therefore, unavailable in a practical sense to the athlete who has not as yet suffered such an injury or has, hopefully, recovered from one. In either instance, the quality of the athlets's performance will suffer due to his knowledge of the pain involved and the negative effect on his career resulting from such knee injury.

DISCLOSURE OF THE INVENTION

It is therefore an object of the present invention to provide an improved athletic knee protector.

Another object is to provide a knee protector which will have a rigid covering across the knee pad and along both sides of the knee.

A further object is the provision of an athletic knee protector which has a rigid part which can be manually formed to fit a variety of sizes and shapes of knees.

Yet another object is to provide a knee protector which can be manually formed to curve comfortably both above and below the kneecap to suit the individual user.

Still another object is the provision of an athletic knee protector which, if bent out of shape while in use, can be quickly and conveniently reshaped to suit the user.

Yet a further object is to provide a knee protector which includes paraphernalia for holding it generally in place over the knee, while allowing some movement as the knee goes from extreme flex to no flex.

Still a further object is the provision of an athletic knee protector which is light weight, strong and easy to manufacture and distribute.

More generally, it is an object of the instant ivention to provide an athletic knee protector which is comprised of an aluminum shield member, oval in shape when flat, but bent to generally "U"-shape along its longer axis, convexly curved in its central portion along its shorter axis, having a first layer of foam rubber on its concave face and being covered with a second layer of protective coating about all faces and edges. The knee protector is held in place over the knee by fitting within an upwardly oriented pocket sewn within the pant leg at knee level of knee-length pants made of two-way stretch material; a flap attached along a line above the opening of the pocket; and two elongated straps attached to the flap and long enough to be brought across the central portion of the pocket, out an opening in the pants just below the pocket, crossed back and forth about the leg, down under the foot, and crossed back up the sides of the legs to be wrapped about the thigh above the rigid portion of the shield, and tied behind the leg approximately at knee level. The strap is hidden from view and held in place by conventional knee-high socks and shoes.

These and other objects, advantages and novel features of the present invention will become apparent from the following detailed description of the invention when considered in conjunction with the accompanying drawings.

BRIEF DESCRIPTION OF THE DRAWINGS

FIG. 1 is a front elevational view of the invention installed on a leg.

FIG. 2 is a side elevational view of the invention installed on a leg.

FIG. 3 is an enlarged perspective view of the shield element of the invention with a portion thereof broken away.

FIG. 4 is a partial enlarged cross-sectional view of the invention taken generally along the line 4—4 of FIG. 1.

FIG. 5 is a partial enlarged cross-sectional view of the invention taken along the line 5—5 of FIG. 2.

BEST MODE FOR CARRYING OUT THE INVENTION

Referring now to the drawings, in which identical or corresponding parts are indicated by the same reference character throughout the several views, and more particularly to FIGS. 1 and 2, the athletic knee protector of this invention is designated generally at 10 and shown in said Figures, installed upon the leg. Athletic knee protector 10 is comprised of a rigid shield assembly, designated generally at 20; a pocket assembly, designated generally at 30, and best seen in FIGS. 4 and 5; and a strap assembly, designated generally at 40.

Referring now to FIG. 3, the core 21 of rigid shield assembly 20 is made of a generally rigid material which is both capable of being bent to suit the individual user by manual manipulation to the desired configuration and flexible enough to return to that configuration when subjected to a limited amount of deforming pressure. Aluminum in the range of 10 gauge thickness is one material which has such properties. Core 21 is cut in an elongated oval shape and then bent into the form of a "U" along the longer axis of the oval shape. It is possible to open the "U" through manual manipulation to fit a large knee or, conversely, to narrow the "U" for a small knee. Likewise it is possible to manually bend the upper and lower edges 22 and 23, respectively, which are parallel to the longer axis of the oval shape near its center 24, in order to create a convexity where rigid shield 20 is adjacent to the kneecap (See also FIG. 5). As can best be seen in FIG. 5, the wings 26 of rigid shield 20 extend past the mid-point of the sides of the femur bone.

A pad 27 of resilient material, such as foam rubber, is bonded to the inner or concave side of core 21. Finally, a smooth covering 28 of somewhat flexible, tough material, such as plastic, is bonded to all exterior surfaces and edges of shield 20 in order to soften its exterior and to maintain the bond between pad 27 and core 21. It has been found that an adequate covering 28 is also provided by wrapping with duct tape. Rigid shield 20, when constructed in the manner described and maintained at kneecap level as the leg flexes, will absorb the shock of hard blows and sudden twists in enough instances that the risk of serious knee injury is greatly diminished.

Pocket assembly 30 and strap assembly 40 together achieve the goal of holding rigid shield 20 in proper position over the kneecap and femur bone area. Referring again to FIGS. 4 and 5, pocket assembly 30 is comprised of two-way stretch pants 31 of the type commonly used in American football and two-way stretch pocket 32. Pocket 32 extends past the midpoint of the femur bone on both sides of the leg and is sewn to the inside of pants 31 along its entire perimeter with the exception of its upwardly oriented edge 33. It is curved at its lower corners 34 to prevent shield 20 from twisting horizontally.

Strap assembly 40 includes flap 41 and double strap 42, both also made of two-way stretch material. Flap 41 is generally rectangular, slightly narrower than the kneecap, and sewn across its upper edge to the inside of pants 31 just above upwardly oriented edge 33 of pocket 30. Flap 41 is long enough to clearly cover edge 31, but not so long that it will stretch below lower edge 36 of pocket 30. At either lower coner 43 of flap 41 is attached a strap element 44 of double strap 42. Strap elements 44 are long enough to be wrapped about the leg, under the foot, back up the leg, around the thigh above shield 20 and tied behind the leg as will be explained shortly.

A small oval-shaped opening 46 is located between lower edge 36 of pocket 30 and lower edge 37 of pants 31. The long axis of opening 46 is horizontally oriented. Double straps 42 are pulled through opening 46 so as to be exposed outside of pants 31 and to be kept centered below the kneecap. After flap 41 and double strap 42 have been pulled far enough above pocket 30 to permit the insertion of shield 20 into pocket 30 and the user has put on pants 31, double straps 42 are pulled tautly downwardly in order to secure shield 20 at kneecap level. Each element 44 is then pulled down the front of the leg and crossed under the foot just in front of the heel pad. If desired, elements 44 may be crossed behind the leg and then again in front before being crossed under the foot. Elements 44 are then crossed in front of the leg before being crossed behind the knee and wrapped about the thigh from either side.

Shield 20 is sufficiently thick that its upper edge 22 provides a ledge for keeping strap elements 44 from slipping below the kneecap. Elements 44 are then tied behind the leg at knee level. It should be obvious that other minor variations in wrapping strap 42 about the leg are possible to suit the user. Finally conventional knee length socks and shoes will assist in maintaining strap 42, and hence shield 20, in place, as well as substantially hiding knee protector 10 from view.

By the use of stretch fabrics having the right amount of resistance to stretch, shield 20 will be allowed to float vertically very slightly about the kneecap as the knee is flexed and straightened between extremes. Yet shield 20 will remain substantially over the kneecap throughout the athletic contest with but little need for adjustments. Core 21 is rigid enough to eliminate most of the unnatural twisting which usually stretches and tears ligaments, yet it will give enough not to be itself the cause of bone breaks. If it is forced out of shape it can easily be manually re-shaped in a brief moment during the contest without need for removal.

Obviously, many other modifications or variations of the present invention are possible in light of the above teachings. It is therefore to be understood that, within the scope of the appended claims the invention may be practiced otherwise than as specifically described. Besides American football and soccer, athletic protector 10 has application in other endeavors such as, roller skating, ice skating, skiing, hockey, bicycling, baseball, basketball, wrestling, karate and ballet dancing.

What is claimed is:

1. A knee protector, comprising:
   a sheet of rigid material, generally oval in shape, the length of its shorter axis being slightly greater than the vertical dimension of a kneecap and the length of its longer axis being slightly greater than the horizontal distance from a point beyond the midpoint of one side of the femur around the kneecap to a point beyond the midpoint of the other side of the femur:
   wherein said material is curved along its longer axis so as to fit over and follow the general contour of the front and sides of the knee; and
   means for holding the central portion of said sheet of material substantially over the kneecap,
   wherein said material holding means includes:
   knee-length pants of stretch fabric tailored to fit snugly in the vicinity of the knee;
   a pocket inside the leg of said pants located and sized to hold said sheet of material substantially over the kneecap, said pocket being open along it upper edge for the insertion of said sheet of material;
   a flap having a first end attached inside the leg of said pants along a line just above and parallel to the opening of the pocket; and
   means for holding the second end of said flap downwardly against said pocket so as to be generally fixed in position with respect to the lower leg, independent of said pants.

2. The knee protector of claim 1, wherein said flap holding means includes two elongated straps of generally stable longitudinal dimension attached to said flap at their first ends and of a length which allows them to be brought under the foot, back up to behind the leg even with the kneecap, around the leg so as to be supported by the upper edge of said sheet of rigid material, and tied together by their second ends behind the leg even with the kneecap and means for bringing said straps under the foot, back up to behind the leg even with the kneecap, around the leg so as to be supported by the upper edge of said sheet of rigid material, and tied together by their second ends behind the leg even with the kneecap.

3. The knee protector of claim 1, wherein said flap holding means includes an opening in said pants just below said pocket and two elongated straps of generally stable longitudinal dimension attached to said flap at their first ends and of a length which allows them to be brought through the opening, under the foot, back up to behind the leg even with the kneecap, around the leg so as to be supported by the upper edge of said sheet of rigid material, and tied together by their second ends behind the leg even with the kneecap and means for bringing said straps through the opening, under the foot, back up to behind the leg even with the kneecap, around the leg so as to be supported by the upper edge of said sheet of rigid material, and tied together by their second ends behind the leg even with the kneecap.

* * * * *